(12) United States Patent
Mörmann et al.

(10) Patent No.: US 10,159,547 B2
(45) Date of Patent: Dec. 25, 2018

(54) MEASURING APPARATUS AND METHOD FOR THREE-DIMENSIONAL MEASUREMENT OF AN ORAL CAVITY

(71) Applicant: Quarz Partners AG, Zurich (CH)

(72) Inventors: Werner Mörmann, Zurich (CH); Albert Mehl, Baar (CH)

(73) Assignee: Quarz Partners AG, Zurich (CH)

(*) Notice: Subject to any disclaimer, the term of this patent is extended or adjusted under 35 U.S.C. 154(b) by 36 days.

(21) Appl. No.: 15/317,826

(22) PCT Filed: Jun. 8, 2015

(86) PCT No.: PCT/CH2015/000086
§ 371 (c)(1),
(2) Date: Dec. 9, 2016

(87) PCT Pub. No.: WO2015/188286
PCT Pub. Date: Dec. 17, 2015

(65) Prior Publication Data
US 2017/0119505 A1    May 4, 2017

(30) Foreign Application Priority Data

Jun. 11, 2014 (CH) .................................. 0884/14

(51) Int. Cl.
*A61C 9/00* (2006.01)
*A61B 1/24* (2006.01)

(52) U.S. Cl.
CPC .............. *A61C 9/008* (2013.01); *A61B 1/24* (2013.01); *A61C 9/006* (2013.01); *A61C 9/0053* (2013.01); *A61C 9/0066* (2013.01); *A61C 9/0073* (2013.01)

(58) Field of Classification Search
CPC ....... A61C 9/006; A61C 9/0073; A61C 9/004; A61C 9/0046; A61C 9/0053; A61C 9/0066
(Continued)

(56) References Cited

U.S. PATENT DOCUMENTS

| | | | |
|---|---|---|---|
| 3,401,690 | A | 9/1968 | Martin |
| 4,223,417 | A | 9/1980 | Solon |

(Continued)

FOREIGN PATENT DOCUMENTS

| | | |
|---|---|---|
| EP | 0015060 | 9/1980 |
| EP | 2166303 | 3/2010 |

(Continued)

OTHER PUBLICATIONS

S. Reich et al., "Intraoral Optical Impression Systems—An Overview", International Journal of Computerized Dentistry, vol. 16, 2013, pp. 143-162.

(Continued)

Primary Examiner — Christopher W Fulton
(74) Attorney, Agent, or Firm — Cooper & Dunham LLP (57) ABSTRACT

Apparatus for three-dimensionally measuring a row of teeth, having, on a shaft, an autonomously movable measuring head including a central measuring member and at least two lateral measuring members movably interconnected and defining a variable measurement space. The head, placed on a row of teeth, is guided therealong using guiding elements. Measuring units in the measuring members measure structures in the measurement space. Measurements are taken from multiple solid angle positions of the measuring units, the positions being preset in the measuring members, being adjusted by moving the measuring members, being taken by having mirrors move, in a controlled manner, the beam path generated by the measuring units, or being aligned by (Continued)

changing the angular position of the head relative to the shaft in an automatically controlled manner.

39 Claims, 5 Drawing Sheets

(58) Field of Classification Search
USPC .......................................................... 33/514
See application file for complete search history.

(56) References Cited

U.S. PATENT DOCUMENTS

| | | | |
|---|---|---|---|
| 4,611,288 A * | 9/1986 | Duret | A61C 13/0004 700/163 |
| 5,372,502 A * | 12/1994 | Massen | A61C 13/0004 433/215 |
| 5,424,836 A * | 6/1995 | Weise | G01B 11/24 250/559.19 |
| 5,738,678 A | 4/1998 | Patel | |
| 5,745,229 A | 4/1998 | Jung et al. | |
| 6,728,423 B1 * | 4/2004 | Rubbert | A61C 7/00 356/601 |
| 7,013,191 B2 * | 3/2006 | Rubbert | G16H 50/50 700/98 |
| 8,520,925 B2 | 8/2013 | Duret | |
| 9,494,418 B2 * | 11/2016 | Schmidt | A61C 19/04 |
| 2003/0016366 A1 | 1/2003 | Takeda et al. | |
| 2004/0252312 A1 * | 12/2004 | Chen | A61C 9/006 356/603 |
| 2008/0276390 A1 | 11/2008 | Hegemann et al. | |
| 2009/0227875 A1 | 9/2009 | Cao et al. | |
| 2009/0279103 A1 * | 11/2009 | Thiel | A61B 5/0088 356/608 |
| 2009/0306506 A1 * | 12/2009 | Heger | A61C 9/00 600/443 |
| 2010/0189341 A1 * | 7/2010 | Oota | A61B 1/0019 382/154 |
| 2010/0239136 A1 | 9/2010 | Gandyra et al. | |
| 2010/0284589 A1 | 11/2010 | Thiel et al. | |
| 2011/0080576 A1 * | 4/2011 | Thiel | G01B 11/026 356/73 |
| 2013/0108980 A1 | 5/2013 | Leinweber | |
| 2014/0022356 A1 | 1/2014 | Fisker et al. | |
| 2014/0146142 A1 * | 5/2014 | Duret | H04N 13/243 348/47 |
| 2015/0079534 A1 | 5/2015 | Tsuji et al. | |
| 2016/0067018 A1 * | 3/2016 | Korten | A61B 1/051 433/29 |

FOREIGN PATENT DOCUMENTS

| | | | | |
|---|---|---|---|---|
| EP | 2191788 A1 * | 6/2010 | ........... | A61B 5/0088 |
| EP | 2469224 | 6/2012 | | |
| FR | 2979054 | 2/2013 | | |
| WO | 9724587 | 7/1997 | | |
| WO | 2012083967 | 6/2012 | | |
| WO | 2013121605 | 8/2013 | | |

OTHER PUBLICATIONS

A. Ender et al., "Influence of Scanning Strategies on the Accuracy of Digital Intraoral Scanning Systems", International Journal of Computerized Dentistry, vol. 16, 2013, pp. 11-21.

Steffen Leopold et al., "Adaptive Mikrolinsen Basierend auf Ailuminiumnitrid Membranen, Tunable Micro-Lenses based on Aluminum Nitride Membranes", ISBN 978-3-8007-3555-6, vol. 14-16, Oct. 2013, pp. 173-176.

Verena Zuerbig, "AlN/Diamond Membranes for Micro-Opto-Electomechanical Systmes", pp. 104-107.

Search report for Swiss Patent Application No. CH00884/14.

T. Vollborn et al., "Soft Tissue-Preserving Computer-Aided Impression: A Novel Concept Using Ultrasonic 3D-Scanning", International Journal of Computerized Dentistry 2014; vol. 17(4), pp. 277-296.

Yueli L. Chen et al., "Optical Coherence Tomography in Dentistry", Selected Topics in Optical Coherence Tomography, Dr. Gangjun Liu (Ed.), ISBN: 978-953-51-0034-8, 2012, pp. 239-260.

Yao-Sheng Hsieh et al., "Dental Optical Coherence Tomography", Sensors 2013, vol. 13, pp. 8928-8949.

Doug Malchow, "Optical Coherence Tomography/Dentistry: Driving OCT Into Dentistry", BioOp-tics World 7/1 (2014), 7 pages.

Steven McDonagh et al., Simultaneous Registration of Multi-View Range Images with Adaptive Kernal Density Estimation, The University of Edinburgh, UK, pp. 1-24. (Rpt. of The Mathematics of Surfaces—XIV Institute of Mathematics and its Aplications, 2013, pp. 31-62).

Dr. Jorg Neugebauer et al., "Digitale Hilfsmittel zur Optimierung Prothetischer Versorgungen", BZB Jul./Aug. 2013, pp. 72-76.

Bernard Koos et al., "Precision of an Instrumentation-based Metheod of Analyzing Occlusion and its Resulting Distribution of Forces in the Dental Arch," J Orofac Orthop, 2010, vol. 71, pp. 403-410.

Sonderforschungsbereich 379 Mikromechnische Sensor-Und Aktorarrays, Mikromechanische Scanner Demonstratoren Anwendung, Scanner, 30 Pages.

Shankar Krishnan et al., "Global Registration of Multiple 3D Point Sets Via Optimization-on-a-Manifold", Eurographics Symposium on Geometry Processing, 2005, pp. 1-11.

* cited by examiner

MEASURING APPARATUS AND METHOD FOR THREE-DIMENSIONAL MEASUREMENT OF AN ORAL CAVITY

CROSS REFERENCE TO RELATED APPLICATIONS

This application is a § 371 national stage of PCT International Application No. PCT/CH2015/000086, filed Jun. 8, 215, claiming priority of Switzerland Patent Application 00884/14, filed Jun. 11, 2014, the contents of each of which are incorporated herein by reference in their entireties.

FIELD OF THE INVENTION

The invention relates to a measuring apparatus for measuring at least a part of an oral cavity, in particular of at least a part of a row of teeth, as well as a corresponding method.

BACKGROUND

An overview of current intraoral 3D-camera systems is found in Int J Comput Dent 2013; 16: 143-162. The cameras described there use an endoscope-type design with a camera body and an access shaft into the mouth, which has an optical window or projectors and sensors at its end. For serial recordings, these cameras are guided freehanded and floating or supported over the row of teeth. According to experience, these known scanners are suited for the measurement of partial rows of teeth.

Application problems exist with scanners of this type when acquiring data from poorly visible surface parts, e.g. for interdental to mesial or distal-oriented natural tooth surfaces as well as for fine-detailed, partly vertical geometrical preparation surfaces. This applies also for the measurement of surfaces situated in the interdental spaces below the tooth equator because the possible jaw and mouth opening limits the alignment of the camera's viewing direction with its rigid endoscope shaft in particular in the region of the molar. Thereby, a complete measurement of the poorly visible surfaces of the rows of teeth is impeded by the manual alignment of the required viewing angles with the conventional construction of these cameras.

Particularly difficult is the acquisition of interdental buccal and lingual lateral surfaces, because it requires freehanded roll- and tilt-movements of the camera simultaneously with a floating movement along the rows of teeth. In addition, the camera needs to be moved within the range of depth of focus. Simultaneously, the soft parts of the cheeks and tongue need to be kept out of the measurement area and the salivation needs to be controlled.

For the mentioned reasons, a complete measurement of the rows of teeth of the complete dentition including the fully or partially toothed upper and lower jaws and a measurement of the palatine as well as of edentulous jaws is particularly complex with the known systems. The complete measurement of the dentition is important for the manufacturing of prosthetic reconstructions and prostheses as well as in orthodontics for the planning and the monitoring of the therapy. Therefore, the user should be enabled to execute the measurements as easily and quickly as possible. It is thereby desired that the measuring system of the camera is designed in such a way that it is adaptable during scanning of the rows of teeth to the varying anatomic topology of the jaws at complete, partial or fully edentulous dentition, and that the measurement is executed from different solid angles fully automatically by itself and thereby freeing the user from manually tuning the difficult solid-angle-adjustments of the camera needed to get a complete measurement.

DISCLOSURE OF THE INVENTION

Hence, the problem to be solved is to provide a method and a measuring apparatus of the type mentioned above that allow an efficient, complete measurement of the oral cavity and in particular of a row of teeth or parts of a row of teeth. The term 'row of teeth' in this context refers to the alveolar ridge including the palate, either complete with teeth or partially or fully edentulous. The measurement is to be carried out over a part of the jaw, in particular over at least one tooth, over half a jaw, or over an entire jaw, and should also be able to record the terminal bite as well as the articulation movements of the lower jaw in relation to the upper jaw.

This problem is solved by the apparatus and method of the independent claims.

According to a first aspect, the invention therefore relates to a measurement apparatus for measuring at least a part of an oral cavity, in particular at least a part of a row of teeth, with a measuring head. The measuring head thereby comprises at least the following elements:

- At least two measuring units, wherein each measuring unit comprises a measuring zone and wherein the measuring zones can be arranged in such a way that they record different areas of a part of a row of teeth, and
- A carrier, which carries the measuring units.

According to the claim, the relative arrangement of the measuring zones of at least two of said mentioned measuring units is adjustable. The invention thereby includes several options for adjustment, in particular: a) by means of changing the shape of the carrier, e.g., by deforming the carrier or by means of movable mechanics/hinges the relative arrangement of the measuring units with respect to each other can be adjusted which in turn alters the arrangement of the measuring zones as well; b) by means of moving the measuring units themselves, e.g., by means of actuators etc. the measuring zones can also be changed on the otherwise unchanged carrier; and c) by changing the measurement zone of individual measuring units, e.g. by changing the position of a mirror, while otherwise the orientation of the measurement units stays unaltered.

The claimed "measurement" preferably relates to a three-dimensional measurement of the surface.

However, color information can also be recorded. For example, the color images in the form of a texture can be superimposed onto the 3D-surface to enable a photo-realistic rendering of the intraoral situation. This preferred embodiment should also always be kept in mind throughout the further description and the claims.

Furthermore, in addition to the three-dimensional recording of the surface, measurements into the depth of the structures can also be carried out by means of the measuring units. For this, e.g. OCT (optical coherence tomography) and/or ultrasound techniques can be applied, which in addition to the 3D-surface also record layers underneath the 3D-surface, and are thus able to provide additional information about the object. Methods for the ultrasonic measuring techniques are, e.g. described in Vollborn et al., 2014 (Ref. 1), and methods in the dental field concerning OCT in Chen et al., 2012 (Ref. 2), Hsieh et al., 2013 (Ref. 3) and Malchow, 2014 (Ref. 4).

The apparatus is designed such that at least a part of the oral cavity can be measured thereby. This, in particular, comprises parts of a jaw and/or the surrounding structures, particularly parts of a row of teeth. Thus, e.g. tooth surfaces, single teeth, teeth with circumjacent soft tissue (fixed and mobile mucosa), segments of the dentition with several teeth or the complete row of teeth in the upper and lower jaw can be measured. In addition, e.g. also the palate can be measured, and/or parts of the upper and lower jaw can be measured simultaneously, e.g. in the form of a buccal scan or of a series of buccal scans during the articulation.

Thanks to the invention, regions can also be recorded that are only difficult to measure with conventional methods, e.g. proximal regions between two teeth or between a preparation and neighboring teeth, cavities of complex preparations as they are required, e.g. for fillings, inlays, onlays, partial crowns as well as endo-crowns, regions of oral mucosa and gaps between teeth and, in general, oral mucosa surfaces free of teeth, including the entire area of the palate area.

A "measuring unit" (also called a "measuring means") is to be understood as a measuring component that is able to three-dimensionally record at least one surface in a measuring zone. In this context, all types, e.g., of the 3D-measurement, such as stereo-photogrammetry, structured illumination, confocal methods, interferometry methods such as white light or speckle-interferometry, optical coherence tomography (OCT) (Refs. 2 - 4) and also ultrasonic 3D-scanning (Ref. 1) can be considered.

A measuring unit can, e.g. comprise a camera with camera optics and an illumination with structured projection optics in order to carry out a 3D measurement. Likewise, as an example for a measuring unit, the stereo arrangement of two cameras is mentioned. Also, a module based on a confocal, interferometric, or OCT method can serve as a measuring unit.

For finding correspondences in the offset images, distinct structures of the surface can then be analyzed, as they, e.g. result from an image under illumination with white LED light, but also from a sequence of images with LEDs of different wavelengths that are sequentially operated.

To keep the measuring time short, such that no blurring occurs during measuring, high-speed cameras can also be used.

Preferably, the measuring unit is miniaturized, whereby a compact intraoral spatial arrangement and high flexibility are achieved. Camera-arrays and projector arrays as well as micro-mirror-arrays are to be mentioned as examples here, each of which form arrays of measuring units; furthermore, micro-cameras with dimensions of 1×1×2 mm are known (e.g. of the company Awaiba).

Each measuring unit is characterized by parameters such as range of measuring depth and range of lateral measurement, resolution, speed of recording, etc. These parameters need to be adjusted to the particular type of embodiment of the invention.

According to the claims, several measuring units are arranged on a common carrier such that, e.g. teeth, larger sections of rows of teeth or an entire row of teeth of one jaw can be measured all at once, preferably from different views. For that matter, there is no need for all the measuring units to be identical; rather, e.g. their size may vary from measuring unit to measuring unit on the carrier. It is also conceivable to combine measuring units with different measuring methods on the carrier.

According to the claims the relative arrangement of the measuring zones of at least two measuring units is adjustable. It shall be understood that "arrangement" means the position and/or the orientation of the measuring zones. In other words, the measuring zones of the measuring units can be brought into different relative positions and/or orientations to each other and thus be adapted to different measuring requirements.

The carrier can advantageously be brought at least into a first and a second configuration, wherein the relative arrangements of the measuring zones of at least two of the measuring units differ in the first and second configurations. By choosing the configuration of the carrier, the arrangements of the measuring zones can be adapted to the surface to be measured. Thus, the carrier can be adapted, before or during the measuring procedure, to the morphological circumstances.

The carrier can, e.g., comprise at least two movably interconnected measuring members, wherein at least one measuring unit is located at each measuring member. By adjusting the measuring members with respect to each other, the arrangement of the measuring zones can be varied.

The carrier can also consist at least partially of a plastically or elastically deformable material by means of which it can be reversibly transformed at least from the first into the second configuration and from the second into the first configuration. For example, the carrier can be elastically extendable like a rubber-type material, wherein the measuring units are introduced into the material. Also, a foil can be considered as carrier, which foil is shaped by hand and held during the measuring procedure. As an analogous example, the registration of tooth contacts with the help of the T-Scan (Ref. 7, 8) sensor foil while closing the jaws to their final position is mentioned.

Preferably, the carrier comprises micro-joints or hinge axes, which allow for a great flexibility and adaptability. The hinges can be provided with springs for an elastic resetting, with a snap-in mechanism for snapping into defined positions, and/or with micro-motors for an automatic adjustment.

Thus, the measuring units are advantageously provided to be movable with or against each other, be it directly via tilting movements of the measuring units or of parts of the measuring units themselves, or indirectly by means of a configurability of the carrier. There is no necessity for a fixed relation in terms of orientation or measuring space between the single measuring units.

Instead of moving the entire measuring unit, only the optical path of the measuring units can be changed via mirrors, in particular via micro-mirror-arrays (Ref. 9). Other components of the measuring units can also be designed adjustable, when these components enable a variation of the optical path and therefore of the measuring zone.

In comparison to conventional techniques, thus, the possibility exists to capture individually different sections of the jaw, deep cavities, proximal areas, or also sections of oral mucosa, both with the same apparatus and also in a single measuring procedure, which significantly increases the field of application and the user friendliness.

The measuring units record different sections of the surface to be measured. It is advantageous if the measuring zones of the measuring units overlap partially. However, this is not a necessary requirement. The acquisition of the entire surface can also be effected by moving or displacing the entire apparatus or by tilting of the single measuring units. The thereby produced single partial 3D-recordings of the surface can, e.g. subsequently be stitched to a global view by methods like the global registration (Krishnan et al. 2005, Ref. 5; Fisher and McDonagh 2013, Ref. 6). Thereby, the mutual spatial allocation of the single views need not be known a priori.

During the analysis of the recordings, it can also be detected whether certain areas of the surface have not yet been acquired. If this is the case, feedback can be provided to the user, whereupon he can repeat the recording in the specific area.

In a further advantageous embodiment the measuring apparatus comprises a shaft for introduction into the oral cavity, which holds a measuring head at its end. Advantageously, the measuring head is movably connected with the shaft.

The measuring head forms the mentioned carrier and carries the measuring units.

Advantageously, the measuring head comprises at least two, particularly three or more measuring members, which are movable with respect to each other and with respect to the shaft.

The carrier can at least partially be made of a shapeable and extendible and contractile material with resetting properties, upon which the measuring units can be oriented in terms of their angular orientation with respect to the row of teeth and in terms of their distance from each other in the spatial axes X, Y and Z to suit the measuring needs.

According to the claims, there exists therefore no fixed spatial relationship between the measuring zones of the measuring units. Such an apparatus can adapt either automatically or by manual manipulation to any topology of the row of teeth.

For example, a central measuring member connected to the shaft as well as two lateral measuring members movably connected on the central measuring member can form the carrier. In this case, the configuration of the carrier can be adjusted by pivoting the lateral measuring members with respect to the central measuring member. This allows to adapt the measuring head to different jaw topologies and to measure the row of teeth from different and variable solid angles.

The measuring means arranged in the central and in both lateral measuring members conduce to three-dimensionally measure a section of the row of teeth which is located inside the measuring space.

If the measuring apparatus comprises a shaft, the shaft can be fixedly or movably connected with the central measuring member. By means of the shaft, the measuring head can be guided along the row of teeth in contact with the row of teeth or contact-free.

The measuring head defines a measuring space, in which the structures of the palate can be measured. Advantageously, this measuring space is open on both sides along an axis X. At least in one configuration of the carrier, the measuring space is confined on both sides along an axis Y by the measuring head and it is open on one side along an axis Z and confined by the measuring head on one side. Here, the axes X, Y and Z stand orthogonal on each other.

If the carrier consists of the mentioned lateral measuring members and the central measuring member, in the mentioned configuration the lateral measuring members confine the carrier on both sides in the direction of the axis Y, and the central measuring member confines the measuring space on one side in direction of the axis Z.

Advantageously, the measuring head comprises the following elements:

At least two lateral guiding members with guiding zones for laterally abutting on the row of teeth and at least two lateral measuring members, whereby at least a part of the measuring units is arranged in the lateral measuring members, advantageously, in this case, the measuring head is configured or configurable such that the distance along the axis Z between the guiding zones of the guiding members from a part of the measuring member which confines the measuring space along the axis Z is between 5 and 20 mm, and along the axis Y the clearance (Dy) of the guiding zones of the lateral guiding members with respect to each other is between 10 and 24 mm, particularly 14 and 22 mm.

In a further preferred embodiment, the lateral measuring members and/or the lateral guiding members are arranged pivoting with respect to each other, and particularly the lateral measuring members and/or the lateral guiding members can be pivoted with respect to each other by at least 30°, in particular at least 90° pivoting, such that the measuring space can be adapted flexibly to the particular requirements.

In a further aspect, the invention relates to a measuring apparatus, in particular of the type described above, for measuring at least a part of a row of teeth comprising a measuring head, which (in at least one of the configurations) defines a measuring space which is open along an axis X on both sides, confined on both sides along an axis Y by the measuring head and is along an axis Z open to one side and confined to the other side by the measuring head, wherein the axes X, Y and Z are arranged orthogonally with respect to each other and, measuring units for three-dimensionally measuring a section of the row of teeth located in the measuring space, wherein the measuring head comprises:

at least two lateral guiding members with guiding zones to laterally abut on the row of teeth and, at least two lateral measuring members, wherein at least a part of the measuring units is arranged in the lateral measuring members.

Advantageously, the measuring head is configured or configurable such (i.e. in at least one configuration designed in such a way) that along the axis Z the distance from the guiding zones and a part of the measuring member which confines the measuring space along the axis Z is between 5 and 20 mm and along the axis Y the clearance of the guiding zones of the lateral guiding members from each other is between 10 and 24 mm, particularly 14 and 22 mm.

In a further preferred embodiment of the first two aspects of the invention, the measuring apparatus comprises a support suited to support the measuring head on a row of teeth as well as a tilting actuator, with which the carrier can be tilted with respect to the support automatically (i.e. electronically controlled). This allows moving the carrier during a measurement, whereby more recordings or recordings from better viewing angles can be generated. Advantageously, the support is connected fixedly with a shaft of the measuring apparatus, with which the user can guide the measuring apparatus.

In a further aspect, the invention relates to a method to measure at least a part of an oral cavity, in particular at least a section of a row of teeth with a measuring apparatus of the above-described type. The method comprises the following steps:

a) Positioning of the measuring head in such a way above a structure of the oral cavity, in particular above a row of teeth, such that a section of the structure gets to be located in the measuring space, and particularly wherein the measuring members at least with their lateral guiding members get in contact with the row of teeth, and b) guiding the measuring head along the structure, in particular in such a way that at least one lateral guiding member stays in contact with the row of teeth, c) measuring the structure, in particular during guiding of the measuring head.

Advantageously, the measuring apparatus comprises a shaft, on which the user holds the measuring apparatus while measuring the row of teeth. Furthermore, it comprises an electronically controlled tilting actuator to tilt the measuring head around at least one axis relative to the shaft. In this case, while measuring the structure, the measuring head can be tilted into different positions relative to the shaft of the measuring apparatus with the tilting actuator to generate measuring images from different viewing angle positions.

Further, the configuration of the carrier can be varied while guiding the measuring head along the structure to adapt the measuring zone to the configuration of the structure to be recorded. If the measuring head, as mentioned above, comprises a central guiding member and at least two pivoting lateral measuring members arranged at the central guiding member, the angular position of the lateral measuring members can be varied with respect to the central measuring member while guiding the measuring head along the structure.

Preferably, thereby the angular position of the lateral measuring members with respect to the central measuring member is varied while guiding the measuring head along the structure. In particular, while the measuring head is guided along the structure, if contact between at least one of the guiding members of the measuring head and the structure is established, the position of the lateral measuring members can be automatically adapted to the width of the structure, e.g. by means of micro-motors controlled by signals from contact- or distance sensors in the guiding members of the lateral measuring members and by signals from angle sensors in the hinges between the central and the lateral measuring members.

In the context of the guiding of the measuring head along the structure, a complete three-dimensional measurement from different solid angles can be enabled by preset different angular positions of the measuring means with respect to the measuring head and/or by automatically controlled changes of solid angles of the entire measuring head by means of tilting actuators.

To generate measurement recordings from different viewing angle positions without manual changes of direction at the shaft and to thereby get a higher precision and an extended measuring space, while measuring the structure, at least a part of the measuring units can be oriented fixedly in different angular position with respect to the walls of the measuring members, or can be moved into different angular positions, or different viewing angles can also be adjusted by controlled movements of the optical path generated by the measuring units by means of mirrors, or the entire measuring head can be tilted actively at least in one of the axes X, Y, or Z to generate measurement recordings from different solid angle positions. The tilting of the entire measuring head can in particular be effected by means of electronically controlled tilting actuators and in particular automatically.

The guiding of the measuring head along the structure can be carried out continuously with controlled speed or sectionwise. For a continuous guidance, the measuring apparatus advantageously comprises output means, e.g. in the form of optical or acoustic signaling devices which indicate whether the speed of the guidance is correct. For an interval—, i.e. section-wise, guidance the measuring apparatus preferably comprises output means, which indicate when the measuring head is to be moved, i.e. when the next recordings can follow.

For measuring a row of teeth, the measuring head can advantageously be guided with a shaft fixed along the axis X, without settling (i.e. without taking it off the row of teeth) along the row of teeth of a half of the jaw to across the centerline of the jaw. In another advantageous embodiment the measuring head can be guided along the row of teeth of the entire jaw without settling, if the shaft is connected on the upper side of the central measuring member pivoting around the axis Y along the axis X with the measuring head. Thereby the shaft is flipped over the axis Y when crossing the centerline of the jaw each.

In one embodiment the measuring head can, as already described, comprise a central occlusal measuring member, which is suited to contact the row of teeth with its side facing the measuring space. Thereby the central measuring member confines the measuring space along the axis Z and allows to bring the measuring head into a defined position in this direction. If the central measuring member is along the axis X connected to the shaft rigidly or via a tilting actuator, the positioning of the measuring head in the axis Z can be defined by the height of the support at the bottom side of the shaft.

The lateral measuring members can be arranged laterally pivoting or flexible on the central measuring member.

Advantageously both lateral measuring members are at their free edges, i.e. at the edges lying opposite the central measuring member and extending along the axis X, studded with a flexible guiding member made of soft plastic protruding to the row of teeth and suited to make contact with the row of teeth. This lateral guiding member can limit a minimum measuring distance of the lateral measuring member to the row of teeth.

Advantageously, the measuring head comprises at least one contact- or distance-sensor to detect a contact of the measuring head with the oral cavity to be measured, i.e. to detect whether the measuring head touches the oral mucosa or a dental structure. In this case the measuring apparatus is structured such that the configuration of the carrier varies in dependence of the signal of the contact- or distance-sensor whereby the configuration can be adapted to the topology of the to be measured structures.

For example, for this purpose at least one contact- or distance-sensor can be placed on the contact area touching the row of teeth in the lateral guiding member, whose signals can serve as angular control of the lateral measuring members. Thereby the angular movement can be actuated by micro-motors arranged in hinges along the axis X and/or can be controlled by angle sensors arranged in the hinge.

Advantageously in the lateral measuring members at least a part of the measuring means are provided as optical sensors for the three-dimensional measuring of the section of the row of teeth located in the measuring space. A part of these optical sensors is arranged in the central measuring member. This way the row of teeth can be well recorded from the occlusal plane but also laterally.

Advantageously the measuring head comprises at least one true color camera for recording of true color images. Particularly all measuring members feature at least one true color camera. The true color recordings can be used for the rendering of the 3D surface representation, for clinical documentation but also for the determination of color values for the color identification for color selection of the restorative materials. The true color camera can be part of the measuring units for the three-dimensional measuring of the row of teeth, or it can be provided as a separate additional component.

To implement an adjustment of the measuring head to the different width of the rows of teeth or the edentulous alveolar ridges, respectively, as well as to extend the measuring range for the recording of the palatal surface, the habitual bite, and the articulation movements of the lower jaw, the measuring members can be arranged pivoting with respect to each other in a simple embodiment, e.g. by means of hinges or elastic or plastic deformation of a connecting material between the measuring members, such as, e.g. elastomers or metals with resetting property, however, they can, e.g., additionally be structured translationally movable with respect to each other. It is also possible that single measuring units in the measuring members are tilted into different solid angles or translationally moved.

For checking and control of the angular positions of the measuring members with respect to each other, advantageously, angle sensors are provided with which the angular position of the lateral measuring members in relation to the central measuring member can be acquired. By taking the angular positions into account, the measurements carried out by the measuring means in the different parts of the measuring head can be correlated better with each other.

The lateral measuring members are advantageously pivoting from their standard position with 90° internal angle with respect to the central measuring member by at least 20° inwards and at least 90° outwards, in particular around a pivoting axis which runs along the axis X.

In a particularly preferred embodiment, in which the lateral measuring members are arranged pivoting on a central measuring member, the lateral measuring members can at least be pivoted between a first position, in which the internal angles facing the measuring space are at most 90° and a second position in the range of 135°-170°. This position of the lateral measuring members allows to abut the measuring head in the oral vestibule (vestibulum) on the oral mucosa of the alveolar ridges of the closed upper and lower jaw rows of teeth and to measure the closed bite as well as the lateral movements of the lower jaw with respect to the upper jaw. In this position the guiding members at the free end of the lateral-measuring members can serve as supports for the central measuring member, which by the angular position of the lateral measuring members with its measuring means can be brought into an optimum measuring distance and can be stabilized by means of the guiding shaft. This type of measuring makes it possible to use the measuring apparatus also for the spatial measuring of the closed bite of both jaws as well as for the recording of the functional movements of the lower jaw.

Particularly advantageously, the mobility of the lateral measuring members can be used for the measurement of the palate, if the lateral measuring members are pivoted with respect to the central measuring member advantageously so far that the angles α facing the measuring space are at least 200°, e.g. 250°. Thereby, a measuring space is created which can be adjusted to the palatal arch with the aid of guiding members of the lateral measuring members and which generates the prerequisite for a fast and complete measurement of the palate.

Particularly advantageously, an actuation for the angular adjustment between the measuring members can be effected by one micro-motor each arranged in both lateral hinge axes. By means of the micro-motors, also predefined angular positions can be reached.

Particularly advantageously, as mentioned, the micromotor actuated angular position of the lateral measuring members can be controlled by contact- or distance sensors which are arranged in the guiding members of the lateral measuring members. During application of the measuring apparatus the angular positions of the lateral measuring members can be controlled individually in such a way that the clearance for the tilting movements of the measuring head can be taken into account. This way, while scanning along the row of teeth, the angular positions of the lateral measuring members can be adjusted automatically to the different cross sections of the row of teeth or to edentulous alveolar ridges as well as to the palatal arch, respectively.

Advantageously, with a shaft movably affixed to the central measuring member on the upper side of the measuring head, contact sensors are foreseen in the connecting element between the shaft and the central measuring member. If in another embodiment, the shaft is connected to the central measuring member along the axis X, sensors in the support of the shaft can measure the contact with the row of teeth. The support can cover the lower side of the shaft in the range of 14-60 mm. Advantageously, the contact sensors control whether the apparatus is being supported. If there is no contact in the case of an extended tooth space, the angular position of the lateral measuring members can be set into a standard position for a contactless measurement.

Particularly advantageously the three-dimensional measurement of the row of teeth can be accomplished by means of a movable connection of the measuring head with the shaft along the axis X via a tilting actuator. The measuring head can be held movably with respect to the shaft and its support on the row of teeth, particularly with the help of said tilting actuator. The height of the support thereby determines the distance of the central measuring member to the row of teeth. For example, tilting movements around the axes Y and Z allow to bring the complete measuring means of the measuring head into a controlled sequence of different viewing angle positions, whereby in these positions measurement recordings can occur. The tilting actuator can comprise piezo elements. These can be placed in the shaft.

For guiding the measuring apparatus a shaft with a length of at least 40 mm, particularly at least 100 mm length can be foreseen on the measuring head.

In the shaft, as mentioned, the piezo elements of the tilting actuator can be accommodated with sufficient length for large tilting angles. For example, four piezo elements can be arranged crosswise whereby tilting movements around two orthogonal axes, particularly the axes Y and Z, can be generated. The tilting angles can particularly lie between 0.25°-12°, preferably 0.5°-6° degrees.

To provide for a good guidance of the measuring head on the row of teeth and for having the possibility to guide the measuring head across the most strongly curved sections of the row of teeth, the lateral guiding members extend along the axis X preferably over a length of 4-30 mm, particularly over a length of 6-16 mm.

The measuring apparatus can in principle be used for intraorally measuring any structure or movement in the oral cavity. Advantageously, the structure or movement, respectively, is at least a part of a row of teeth, at least a part of an alveolar ridge, a closed bite, the movement of the lower jaw, or at least a part of the palate.

The measuring apparatus can, at least in the area of the hinges between the measuring members, be covered leak-tight against bacteria by an elastomer layer, whereby it can be disinfected efficiently after use on the patient.

BRIEF DESCRIPTION OF THE DRAWINGS

Further embodiments, advantages, and applications of the invention result from the dependent claims and from the following description with reference to the figures. Thereby show:

MODES FOR CARRYING OUT THE INVENTION

Measuring Apparatus

Figure 1:
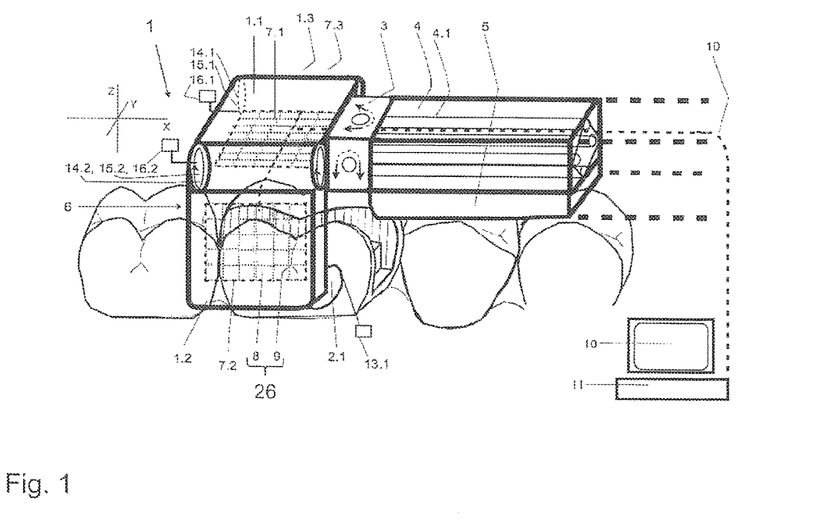
FIG. 1 a schematic sketch, in perspective side view, of a measuring head with a central and two pivoting lateral measuring members, wherein the measuring head is connected movably via a tilting actuator along the axis X with a shaft above a row of teeth, FIG. 2 a schematic cross-sectional representation of the measuring head according to FIG. 1, above a posterior tooth with one central and two pivoting lateral measuring members, FIG. 3 schematic cross-sectional representations of measuring arrangements with a shapeable carrier, which is adapted in a) and d) above a posterior tooth, in b) and e) at the buccal side at the terminal occlusion and articulation, and in c) and f) at the palatal arch to the topology, wherein a) to c) are examples for embodiments of measuring units with projectors and micro cameras, whereas d) to f) are examples for embodiments with arbitrary measuring units, FIG. 4 a schematic sketch in perspective side view, of a measuring head with a central measuring member and two pivoting lateral measuring members, with a guiding shaft movable around the axis Y on the upper side of the central measuring member, FIG. 5 a schematic cross-sectional representation of the measuring head according to FIG. 1 above an anterior tooth with a central and two inwardly rotated lateral measuring units, FIG. 6 an illustration of the measurement of the terminal occlusion of teeth of the upper and lower jaw in cross section with outwardly pivoting lateral measuring members, which laterally support the measuring head on the jaws, FIG. 7 an illustration of the measuring method in a cross-sectional representation of the palate with by 250° outwardly rotated lateral measuring members ($\alpha$=250°), FIG. 8 an illustration of the measuring method in a cross-sectional representation of the edentulous lower jaw with support and guidance of the measuring head on the alveolar ridge with guiding shaft according to FIG. 3 on the left and with guiding shaft according to FIG. 1, on the right, and FIG. 9 a schematic sketch of a measuring unit consisting of a micro projector and a micro camera with micro mirrors and a first and a second measuring zone on a tooth surface.

FIG. 1 shows the embodiment of a measuring apparatus in which a measuring head 1 is connected by a tilting actuator 3 movably with a shaft 4. The measuring head 1 comprises a central measuring member 1.1 and two lateral, pivotingly attached measuring members 1.2, 1.3. For contact with the row of teeth the measuring members 1.1, 1.2, 1.3 feature guiding members 2.1, 2.2, and the shaft 4 is equipped with a support 5 to provide support on the row of teeth. The apparatus is presented schematically in perspective side view above the row of teeth.

The guiding members 2.1, 2.2 are arranged at the free ends of the lateral measuring members 1.2, 1.3 and extend along the axis X.

The measuring members 1.1, 1.2, 1.3 together form the carrier for the measuring units described further down.

With the tilting actuator 3 the carrier 1.1-1.3 can be tilted automatically with respect to the support 5.

The measuring head 1 defines, based on its orientation, a coordinate system with the axes X, Y and Z.

In the presented embodiment according to FIG. 1 the measuring head 1 with its central measuring member 1.1 is connected movably by the tilting actuator 3 pivoting around the axes Y and/or Z to the shaft 4. In the embodiment according to FIG. 1 the shaft 4 extends along the axis X and can be guided with the support 5 on the row of teeth. The height of the support 5 defines the distance of the central measuring member 1.1 from the row of teeth.

The measuring head 1 comprises in the embodiment according to FIG. 1 the central measuring member 1.1 arranged parallel to the occlusal plane and the two lateral measuring members 1.2 and 1.3 arranged pivoting with respect to the central measuring member 1.1, e.g. by means of hinges.

The measuring head 1 defines a measuring space 6 which is open on both sides along the direction of axis X, confined in the direction of the axis Y by the two lateral measuring members 1.2 and 1.3, and confined in the direction of the axis Z by the central measuring member 1.1 on one side and open on the other side. The measuring members 1.1, 1.2 and 1.3 comprise measuring units 26, each of which comprises in the embodiment according to FIGS. 1 and 2 at least one micro projector 8 as well as a micro camera 9.

The lateral guidance of the measuring head can be formed in the present embodiment according to FIG. 1 by the lateral guiding members 2.1, 2.2 which are affixed at the free ends of the measuring members 1.2 and 1.3 facing the row of teeth. On the side of the occlusal plane the guidance is implemented by the support 5.

The lateral measuring members 1.2, 1.3 extend along the axis X, e.g. over 3-20 mm, particularly 4-17 mm. These dimensions enable that the measuring apparatus can be easily guided through the internal curvature in the region of the canine teeth.

In the measuring members 1.1, 1.2 and 1.3 the measuring units 26 are arranged (whereby in this embodiment each single measuring unit comprises at least one micro projector 8 and one micro camera 9), with which the row of teeth can be measured in the measuring space 6, i.e. three-dimensionally acquired. The measuring units 26 (each one comprising a micro projector 8 and a micro camera 9) are e.g. formed as arrays 7.1, 7.2, 7.3 of micro projectors 8 and micro cameras 9. The measuring members 1.1, 1.2 and 1.3 form the carrier for the measuring units 26.

The controlling feed cable 10 to the single measuring units 26 are led through the measuring head 1 and run through the tilting actuator 3 and the shaft 4 to a control unit 11, where on a monitor 12 the combined individual recordings of the measuring units 26 can be presented as a unified complete recording of the row of teeth.

The shaft 4 forms the continuation of the central measuring member 1.1 in direction of the axis X and can supplement it in length by at least 40 mm. The shaft can e.g. be between 40 and 150 mm long, can have an overall height of (in the direction of the axis Z) 5-30 mm and a width of (in the direction of the axis Y) of 10-30 mm. This enables to accommodate long piezo elements 4.1 in the shaft, which as actuators are able to generate defined tilting movements of the tilting actuator 3 at least around the axes Y and Z. Thereby the entire measuring head can be brought into a controlled sequence of different view angle positions, wherein in these positions measurement recordings can occur.

Via the length of the piezo elements, relatively large tilting angles are enabled. For example four piezo elements 4.1 can be arranged crosswise, whereby tilting movements around two axes standing orthogonal with respect to each other, particularly the axes Y and Z, can be generated. The tilting angles can particularly lie between 0.25-12°, preferably 0.5-6°.

The piezo elements 4.1 produce tilting movements around two orthogonal tilting axes, particularly the axes Y and Z, and can optically tune at least 16 mrad tilting angle each. The piezo elements 4.1 can be equipped with integrated position sensors, which allow for high positioning stability and a reproducibility in the sub-grad range. Measuring recordings can be initiated in the end positions of the tiltings, which advantageously enables a controlled, very fine-detailed measuring of the row of teeth.

By generating a plurality of image data from different solid angles, a high accuracy and precision of the three-dimensional measurement can be achieved.

The lateral measuring members 1.2 and 1.3 feature at their free ends one support- and guiding element 2.1, 2.2 each, which during the measuring can laterally abut against the row of teeth or the oral mucosa, respectively. In the embodiment according to FIG. 1 the support- and guiding elements 2.1, 2.2 are made from elastomer and can project above the surface of the measuring members 1.2 and 1.3 facing the measuring space 6 by 1-15 mm to ensure the measuring distance to the row of teeth. The support- and guiding elements 2.1, 2.2 can be equipped with contact- or distance sensors 13.1, 13.2 by what the lateral guidance of the measuring head 1 along the row of teeth and the control of the angles of the lateral measuring members 1.2, 1.3 during the measuring can be ensured. The distances of the lateral measuring members 1.2, 1.3 can be chosen such that the tilting movements are not interfered with during scanning.

For the extension of the measuring space and for the adaptation to different jaw-topologies the angular position of both lateral measuring members 1.2 and 1.3 with respect to the central measuring member 1.1 can be adjusted at the connecting parts e.g. by the hinges 14.1, 14.2 by means of at least one actuator, particularly by means of integrated micro motors 15.1 and 15.2. Thereby the lateral measuring members can be pivoted into predefined positions. Further, the actuator can be controlled by sensors 13.1, 13.2, 16.1, 16.2, particularly contact- or distance sensors 13.1, 13.2 to, e.g. keep the lateral measuring members in predefined distances from a row on the jaw. The sensors can also be formed by of the measuring units 26 (each single e.g. consisting of one micro projector 8 and one micro camera 9).

Figure 2:
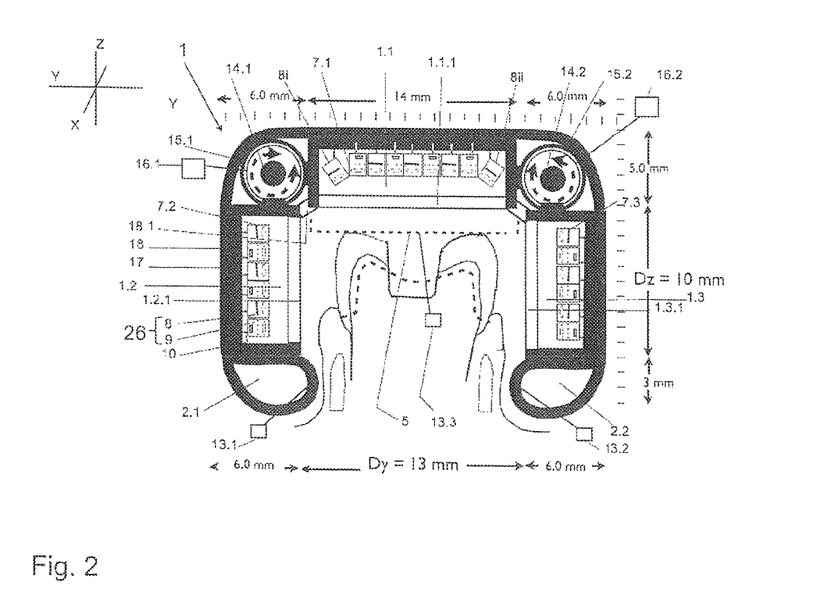

FIG. 2 shows a schematic cross-sectional sketch of the embodiment of the measuring head 1 according to FIG. 1 and illustrates its dimensions. The apparatus can externally in the direction of the axis Y be e.g. between 18-36 mm wide and in the direction of axis Z 10-30 mm high.

The walls 17 of the lateral measuring members 1.2 and 1.3 as well as of the central measuring member 1.1 can e.g. be made of metal and can be connected by the hinges 14.1, 14.2. They constitute the above-mentioned carrier of the measuring head 1. On their internal surfaces, e.g., arrays 7.1 7.2, 7.3 can be arranged, which are made of approximately 1×1 mm sized in cross section and 1.5 mm long alternatingly arranged micro projectors 8 and micro cameras 9. Incoming and outgoing signal lines 10 run to these. Facing the measuring space 6 the measuring members can be sealed by scratchproof optical glass, e.g. sapphire glass.

The adherence to a minimum measuring distance to the occlusal plane between the surface of the measuring units 26 and the surfaces of the rows of teeth of e.g. 1-10 mm is during the measuring ensured by the support 5 of the shaft 4 or in another embodiment by a guiding element 1.1.1 of the central measuring member 1.1 made of scratch-proof optical glass. With the 90° standard angle of the lateral measuring members 1.2 and 1.3 with respect to the central measuring member 1.1, the centering of the measuring head 1 can be effected by the guiding members 2.1 and 2.2 at the free end of the lateral measuring members 1.2 and 1.3. With the 90° standard angle of the lateral measuring members 1.2 and 1.3 with respect to the central measuring member 1.1, the height of the formed measuring space 6 between the measuring-space-facing surface 1.1.1 of the central measuring member 1.1 or from the lower side of the support 5 to the free ends of the measuring members 1.2 and 1.3, respectively, can be between 6 to 14 mm, and the clear width can be between 12 and 24 mm, particularly 14-18 mm. The glass elements 1.1.1, 1.2.1, and 1.3.1, which form the measuring-space-facing endings of the measuring members 1.1, 1.2, 1.3, can ensure a minimum measuring distance between the surface of the measuring units 26 and the surfaces of the rows of teeth of e.g. 1-10 mm.

Figure 3:
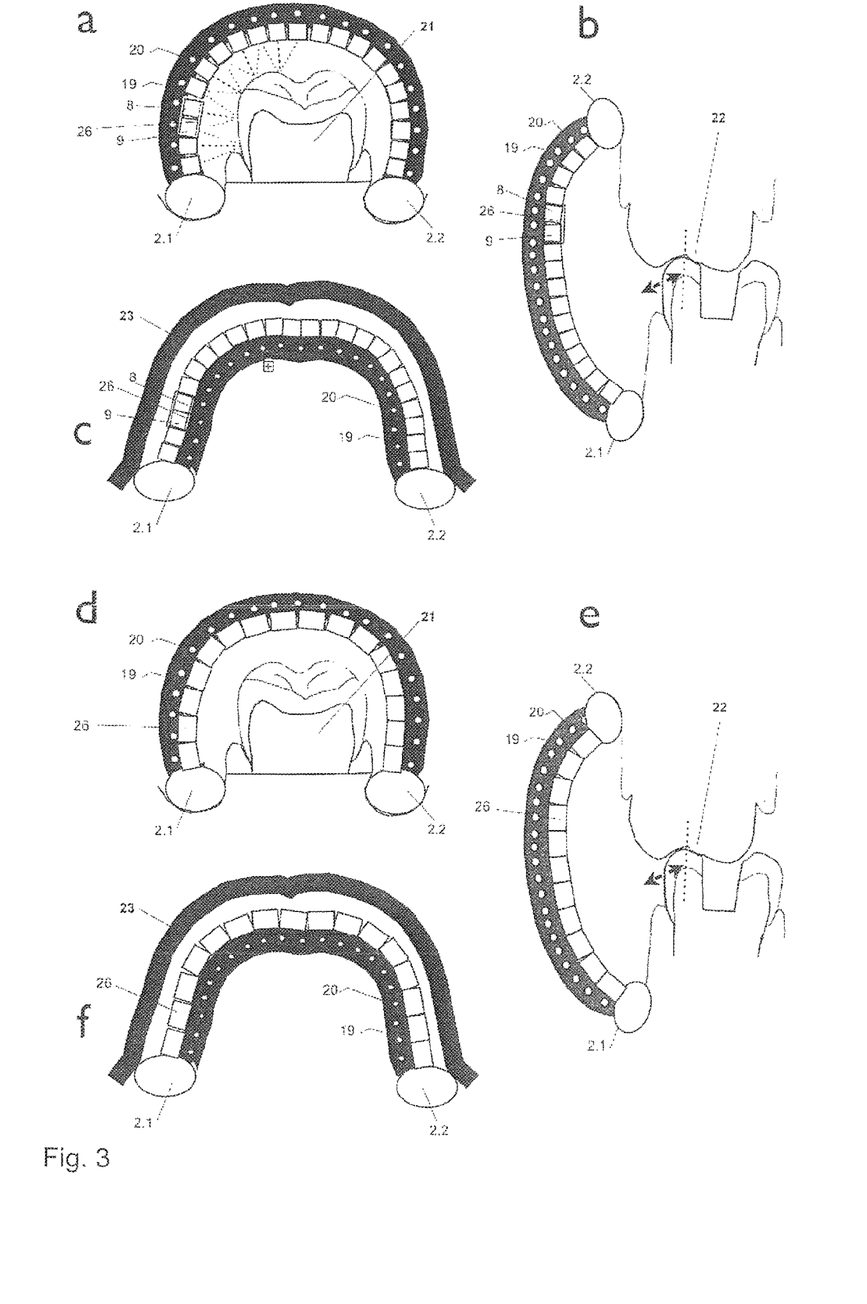
Figure 6:
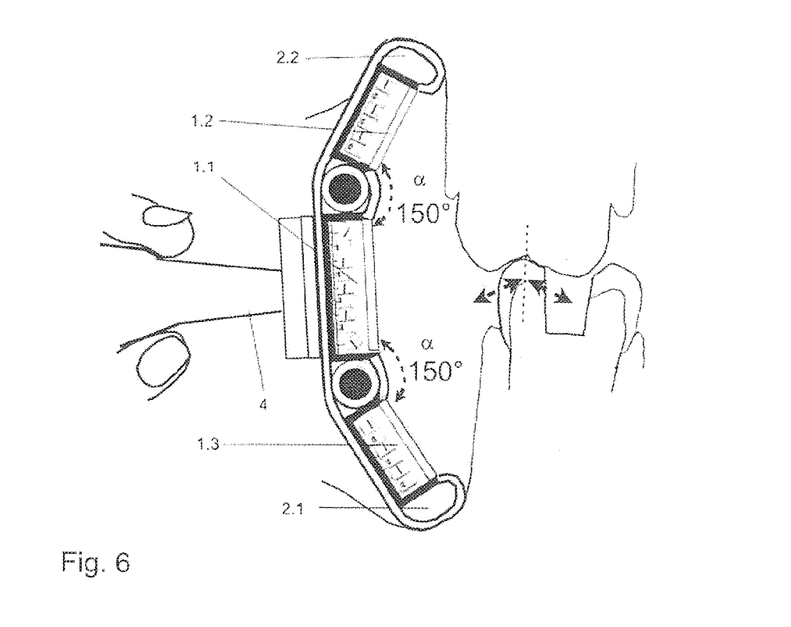
Figure 7:
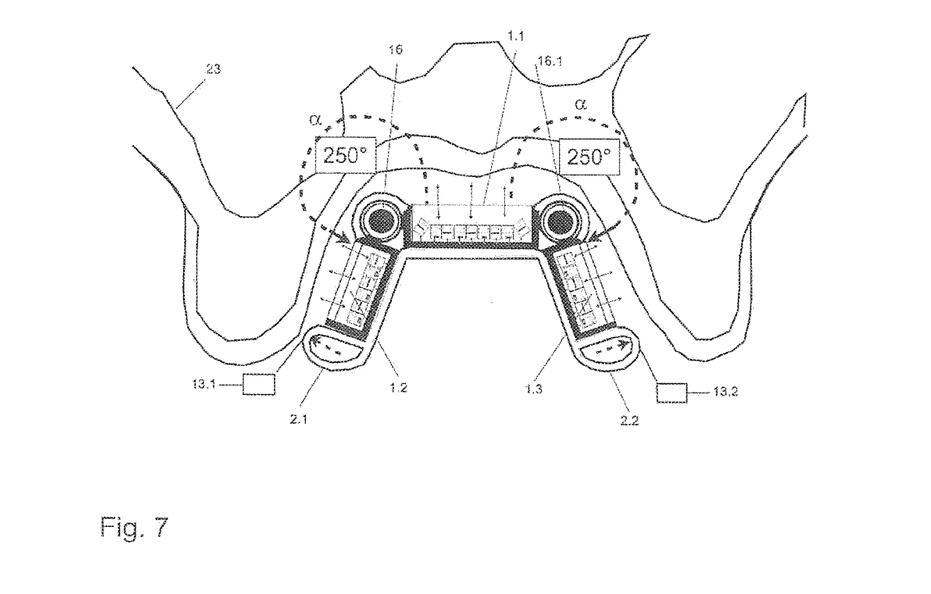
Figure 8:
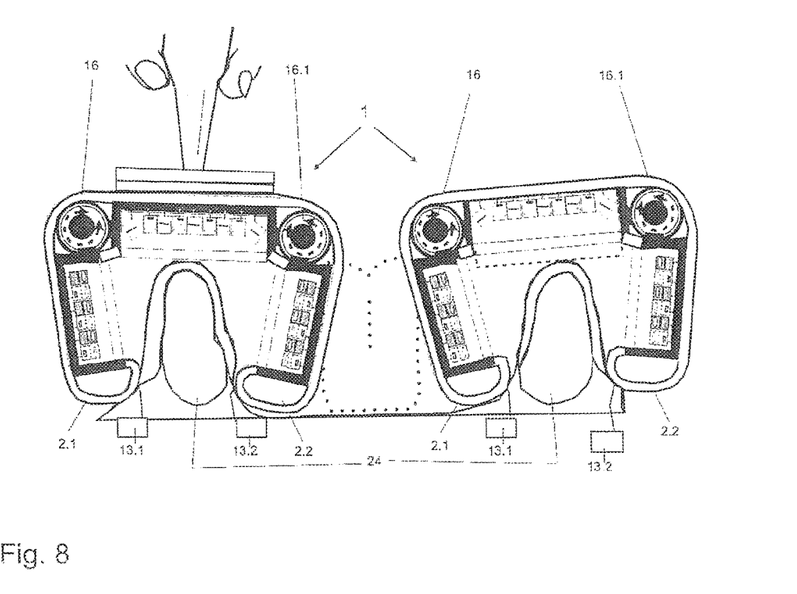

The connecting sites between the measuring members 1.1, 1.2 and 1.3, which are e.g. formed by the hinges 14.1 and 14.2, allow a change of the angular position of the lateral measuring members 1.2 and 1.3 with respect to the central measuring member 1.1 starting from the vertical position shown in FIG. 2. The angles can be adjusted separately or together at least in the range of, e.g. 1-30° inwards (FIG. 4), and 1-170° outwards, i.e. the measuring-space-facing angle α can advantageously at least be adjusted in the range of 60°-200°. Angular positions of the lateral measuring members 1.2 and 1.3 with respect to the central measuring member 1.1 between α=110° to 180° outwards can be used with particular advantage for the measurement of the habitual conclusion of the upper and lower jaw (FIGS. 3, 6). Variations of the angular position up to α=270° of the lateral measuring members with respect to the central measuring member are also suited for the measurement of edentulous upper and lower jaws as well as of the palatal arch (FIGS. 7 and 8). This will be described in more detail further below.

As illustrated by FIG. 2 by means of the micro projectors in positions 8i and 8ii in areas of the central measuring member 1.1 and/or of the lateral measuring members 1.2, 1.3, individual micro projectors and/or micro cameras can be arranged relative to the particular inner surface of the measuring member at an angle unequal to 0 or 90° to allow for a better recording of the structures.

All internal wall areas of the measuring members 1.1, 1.2, 1.3 studded with measuring units 26 can be protected with scratch proof optical glass, e.g. sapphire glass. Thus, the measuring space can be made essentially from this material, which then at the measuring member 1.1 can also fulfill the function as supporting, sliding and guiding element 1.1.1.

To ensure during the guidance of the measuring head above the row of teeth the contact of the guiding members 5, 2.1 and 2.2 with the row of teeth, contact- or distance sensors 13.3 can be arranged in the support 5 as also in the guiding members 2.1 and 2.2 on both sides at the free ends of the lateral measuring members 1.2 and 1.3 (FIG. 2).

The transitions between the lateral measuring members 1.2, 1.3 and the central measuring member 1.1 in the region of the hinges can be completely covered with an elastomer layer 18, 18.1 which tolerates the change of angles of the lateral measuring members 1.2, 1.3 and seals the measuring head on all sides. By means of the closed construction advantageously an efficient disinfection of the measuring head is enabled after use on the patient.

FIG. 3 shows schematic cross-section representations of a measuring apparatus in different configurations based on a shapeable, flexibly adaptable carrier 19, which is adapted to the topology in a) and d) above a posterior tooth 21, in b) and e) at the buccal posterior region with habitual occlusion and articulation 22, and in c) and f) at the palatal arch 23. In the representations a) to c) examples of measuring units 26 with micro projectors and micro cameras can be seen which are aligned according to the topology of the row of teeth, respectively. The guiding members 2.1 and 2.2 can serve as support of the particular configuration of the carrier 19. The white point-shaped elements 20 symbolize flexible elements, e.g. micro joints or hint at the deformability of the carrier material.

In the representations according to FIG. 3 d) to f) again embodiments with single measuring units 26 are shown, which represent any measuring principles (e.g. pairs of stereo-cameras for dual image photogrammetry methods, building blocks for confocal and interferometric methods etc). Thereby not all measuring units 26 must necessarily use identical methods but also measuring units with several measuring principles can be combined on the carrier.

Figure 4:
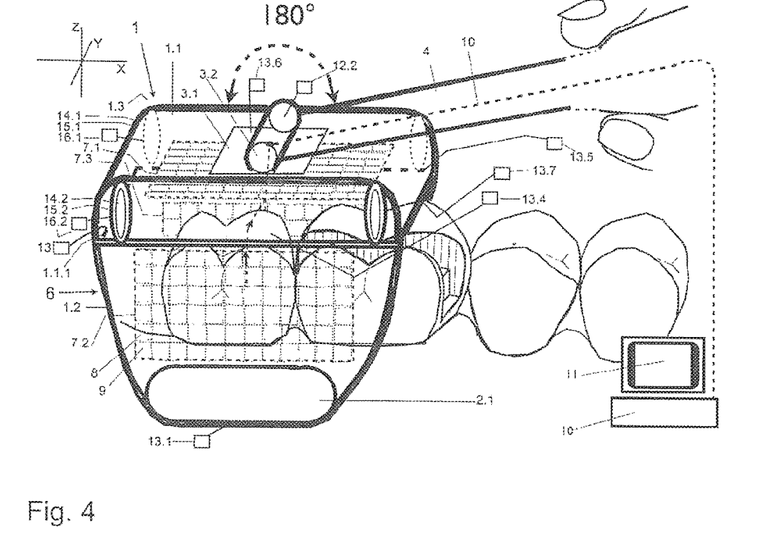

FIG. 4 shows a schematic sketch of a further embodiment of the apparatus. The measuring head 1 of this configuration is connected to a shaft 4 movably around the axis Y. The shaft 4, can e.g. be between 40 150 mm long, can have an overall height (in the direction of the axis Z) of 5-30 mm, and can be wide in the direction of the axis Y, e.g. between 18-36 mm.

The control feed lines 10 to the individual sensor arrays 7.1, 7.2, 7.3, are passed through the measuring head 1 and run through the shaft 4 to a control unit 10, where on a monitor 11 the combined individual recordings of the measuring units 26 can be displayed as a unified complete recording of the row of teeth.

The measuring members 1.1, 1.2 and 1.3 can in turn be equipped with micro-projector-micro-camera-arrays 7.1, 7.2, 7.3 with, e.g. 36 micro projectors 8 each, and 36 micro cameras 9 each, which e.g. can be arranged alternatingly with a cross-sectional dimension of e.g. 1×1 mm, whereby the measuring units 26 can be assembled in the form of arrays continuously or in separate units.

The plurality of the optical measuring units 26 (each individually e.g. consisting of one micro projector 8 and one micro camera 9) allows to orient them within the arrays advantageously line-by-line or column-by-column towards different solid angles, or to use different orientations of the solid angles with subdivided arrays.

All measuring units 26, or also only a part of the measuring units (e.g. a part of the micro projectors 8 and micro cameras 9), can be used for the presentation of the row of teeth and the oral mucosa in true colors. Thereby an as similar as possible to nature esthetic design of the tooth restorations is enabled.

The movability of the shaft 4 with respect to the measuring head 1 around the axis Y by 180° furthermore allows to put the measuring head onto the row of teeth reversed by 180°. This way the measuring head 1 can advantageously be guided in two runs from the left to the right region of the mouth and from the right to the left region of the mouth or vice versa. Thereby, when crossing the centerline of the jaw, the shaft 4 is reversed to the other side, respectively.

If one or more measuring units in the measuring members 1.1, 1.2, 1.3 are positioned in the direction of the axis X with a viewing angle of 2°-45° and the row of teeth is measured in this direction with such a general viewing angle, the measurement can be complemented with a second measuring run with a reversed measuring head 1 and with thereby reversed viewing angle. This way, advantageously, additional image data can be generated. The angular positions of the guiding shaft 4 can be acquired by means of an angle sensor 12.2. The pressure exerted on the measuring head while scanning is acquired by means of a pressure sensor 13.6 in the guiding basis 3.1. Angle and pressure data can be used to control the measuring head by means of a micro motor, e.g. with 4 mm diameter in the connecting part 3.2.

For expansion of the measuring space and adjustment to different anatomic jaw-topologies, the angular position of both lateral measuring members 1.2 and 1.3 with respect to the occlusal measuring member 1.1 can be adjusted by means of the hinges 14.1 and 14.2 by built-in micro motors 15.1, 15.2 with a diameter of, e.g. 4 mm and can be controlled by angle sensors 16.1 and 16.2 respectively.

To enable the contact of the guiding members 1.1.1, 2.1 and 2.2 with the row of teeth during the guiding of the measuring head on the row of teeth, contact- or distance sensors 13 and 13.1 are arranged in the distal and mesial wall parts surrounding the guiding element 1.1.1, and in the lateral frame parts each of the contact- or distance sensors 13.2 and 13.3 are arranged. Further contact- or distance sensors 13.4, 13.5 are arranged in the guiding members 2.1 and 2.2 on both sides at the free ends of the lateral measuring members 1.2 and 1.3 (FIG. 4).

Measuring Units

The measuring units 26 can, as mentioned, at least partially be formed by micro projectors and cameras, operating according to the principle of structured light as, e.g., described in EP 2166303 or EP 2469224.

The miniaturized micro projectors each consist individually or in a system arrangement of light sources, which can be a chromatic LED, a white LED or a laser, or which can be fed by light guides. For the triangulation method both polychromatic and monochromatic light can be used. The light sources of the micro projectors for the projection of single patterns can differ in the wavelength, such that the patterns in simultaneous triangulation recordings from different solid angles can be analyzed independently from each other.

The micro projectors can be equipped with different masks for the creation of different patterns, e.g. striped patterns with different orientations of the stripes. Alternatively, for the projection of the striped patterns they can be designed as image array element projector, which is controlled by a video signal. Advantageously, the micro projector elements can consist of a miniaturized digital DLP pattern generator (Texas Instruments Application Report DLPA026-May 2011) or LCoS-pattern projector and can feature a micro projector optics with one or more lenses.

Advantageously, the micro camera elements consist of a CCD sensor or a CMOS sensor and a micro camera optics of one or several lenses. For example, 'Naneye CSP' camera modules can be used, which feature a 1 mm×1 mm sized CMOS image sensor and can be equipped with a matching miniature optics. Advantageously, these elements are integrated in an array.

The optical path created by the measuring units 26 can be adjusted to different measuring directions by means of pivoting mirrors. For this the measuring units 26 can be arranged in form of micro mirror arrays (Ref. 9).

One advantage of the described procedure of the optical three-dimensional measuring is that on the one hand a single pattern, projected onto the surface of the row of teeth by a micro projector can be simultaneously recorded by several neighboring micro cameras from different solid angles, and the image data can be analyzed independently from each other. On the other hand micro projectors, e.g. four of them, immediately surrounding one micro camera, can simultaneously project color striped patterns in different spectral ranges from different solid angles, which are recorded at the same time by a dedicated micro camera, and which can be analyzed independently from each other at once via binary code. For this, spectrally distinguishable color patterns can be generated, e.g. by the use of filters. In both cases a plurality of image data from different solid angles can be gathered.

Advantageously, the measurements run by the central and lateral measuring units/arrays can occur simultaneously or sequentially.

On the single arrays, measurements run by individual measuring units in the lines and columns can occur simultaneously or sequentially.

Micro projectors and micro cameras can be selectively equipped with optics with different depths of field, whereby the range of the depth of field can be extended and the highest effective resolution of the three-dimensional measurement of the row of teeth can be achieved.

Typically, the miniature optics of the micro-projector-micro-camera-elements exhibit a depth of field range of 1-20 mm.

Particularly advantageously, focus-adaptive lenses can be used for the optical configuration of the measuring units to extend the depth-of-field range.

Instead of (or additionally to) of a measurement by means of structured light, the measurement can be carried out by means of stereoscopic cameras. Also, a combination of triangulation methods and stereoscopic methods can be used. Further, also the confocal laser technology can be applied for the measurement.

Measuring Methods, Applications

Figure 5:
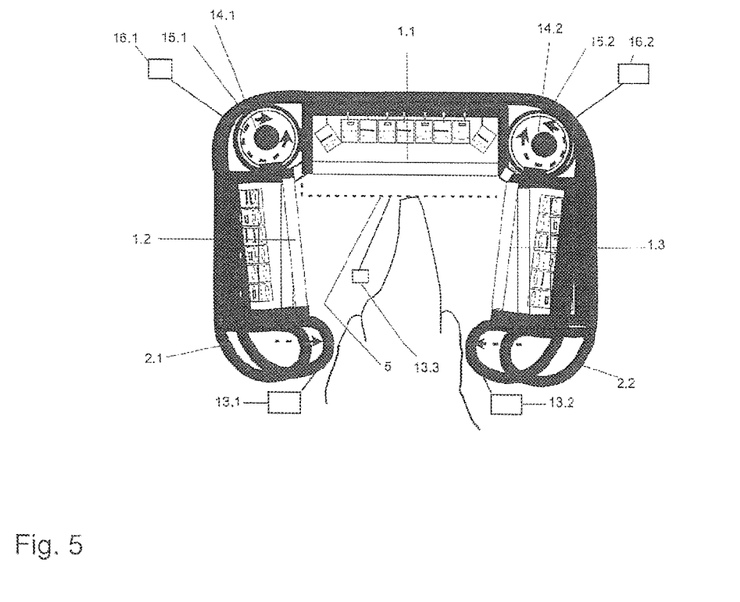

FIG. 5 illustrates a particular application of the apparatus according to FIG. 1 during the measurement of a central anterior tooth with clearly narrower alveolar process compared to the posterior region (FIG. 2). In the representation, e.g. the measuring member 1.2 is pivoted by 6°, and the measuring member 1.3 by 17° inwardly.

FIG. 6 illustrates a particular application of the apparatus during the measurement of the habitual occlusion of both jaws. Represented is the apparatus according to FIG. 4, whereby the carrier (i.e. the measuring members 1.1, 1.2, 1.3) is arranged in a different configuration, though.

The measuring head 1 can be stabilized by simultaneous support of the support elements 2.1 and 2.2 on the oral mucosa of the alveolar processes of the upper and lower jaw by the shaft 4.

The recording activity can be limited to the central array 1.1 in the measuring member 1.1.

During application of the apparatus according to FIG. 1, the measurement can be used either with or also without activation of the tilting mode of the measuring head. The support in each case is provided by the support 5 at the shaft 4 on the buccal surfaces of the row of teeth.

From the represented position also the articulation movements of the lower jaw against the upper jaw can be recorded with a high sequence of images of approx. 18-24 frames per second or more.

FIG. 7 shows the schematic sketch of a cross-section through the edentulous upper jaw 23 during a further application of the measuring method according to the invention.

Here, the carrier (formed by the measuring members 1.1, 1.2, 1.3) is in a convex configuration. The lateral measuring members 1.2 and 1.3 of the measuring head are in this application pivoted according to the arching of the palate by an angle α of, e.g. 250° beyond the plane of the central measuring member until the measuring members are almost parallel to the surface of the palate. The measuring head if applied in the embodiment according to FIG. 1 (with activation of tilting) can be guided across the palate with support on the support 5 of the shaft 4.

During application of the apparatus according to FIG. 4, the measuring head can be brought into contact with the oral mucosa with at least one of the guiding members 2.1 or 2.2 and can be moved translationally as well as rotatingly at the palate until the complete surface is measured. For an optimum support, the lateral measuring members 1.2 and 1.3 with their guiding members 2.1 and 2.2 can be held in full contact during the scan movements along the surface of the palate by means of the contact- or distance sensors 13.1 and 13.2 by means of the control of the micro motors in the hinges. Thereby, advantageously, approximately constant distances for the three-dimensional optical measurement can be created.

The measuring of the complete surface of the palate is crucial both for prosthetic as well as for orthodontic treatments.

FIG. 8 shows the schematic sketch of a cross-section through the edentulous lower jaw 24 in a further application of the optical three-dimensional guided measuring. The measuring can be executed with the measuring head 1 both with the shaft 4 according to FIG. 1 and with the shaft according to FIG. 4. For an optimum support, the lateral measuring members 1.2 and 1.3 with their guiding members 2.1 and 2.2 can provide the guidance of the measuring apparatus during the scan movements along the surface of the entire alveolar ridge of the lower jaw by means of the contact- or distance sensors 13.1 and 13.2 by the control of the micro motors in the hinges.

Figure 9:
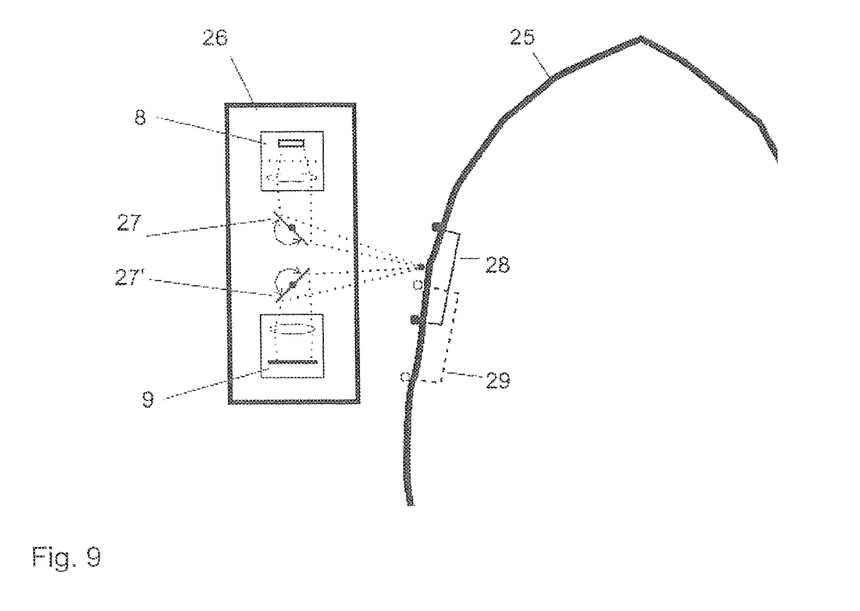

FIG. 9 shows a schematic sketch of a measuring unit 26 consisting of a micro projector 8 and a micro camera 9 with micro mirrors 27, 27' and a first measuring zone 28 as well as a second measuring zone 29 on a tooth surface 25.

This embodiment illustrates that the arrangement of the measuring zone of a measuring unit can be varied also at the time when the carrier of the measuring head does not move.

The embodiment according to FIG. 9 however, can also be combined with a movable, i.e. configurable carrier.

Remarks

While in the present application preferred embodiments of the invention are described, it is clearly pointed out that the invention is not limited to these and can also be implemented in a different way within the scope of the following claims.

References

1. Vollborn T, Habor D, Pekam F C, Heger S, Marotti J, Reich S, Wolfart S, Tinschert J, Radermacher K: Soft tissue-preserving computer-aided impression: a novel concept using ultrasonic 3D-scanning. Int J Comput Dent 2014; 277-96.

2. Yueli L Chen, Quan Zhang and Quing Zhu (2012). Optical Coherence Tomography in Dentistry, Selected Topics in Optical Coherence Tomography, Dr. Gangjun Liu (Ed.), ISBN: 978-953-51-0034-8, InTech, Available from: http://www.intechopen.com/books/selected-topics-in-optical-coherence-tomography/optical-coherencen tomography-in-dentistry 3. Yao-Sheng Hsieh, Yi-Ching Ho, Shyh-Yuan Lee, Ching-Cheng Chuang, Jui-che Tsai, Kun-Feng Lin and Chia-Wei Sun: Dental Optical Coherence Tomography. Sensors 2013, 13, 8928-8949; doi:10.3390/s130708928.

4. Malchow, Doug: Optical Coherence Tomography/Dentistry: Driving OCT into Dentistry. BioOptics World 7/1 (2014).

5. Shankar Krishnan, Pei Yean Lee, John B Moore, Suresh Venkatasubramanian: Optimization-on-a-manifold for global registration of multiple 3D point sets. Eurographics Symposium on Geometry Methoding M. Editors: Desbrun, H. Pottmann, 2005, 1-11.

6. Fisher B, McDonagh S. Simultaneous registration of multi-view range images with adaptive kernel density estimation. In: The Mathematics of Surfaces—XIV. Institute of Mathematics and its Applications. 2013. P. 31-62.

7. Neugebauer J, Kistler S, Elbertzhagen A, Kistler F. Digitale Hilfsmittel zur Optimierung prothetischer Versorgungen. BZB Juli/August 2013: 72-76.

http://www.cumdente.com/fileadmin/user_upload/doc/BZB_7-8-2013_Dr.Neugebauer_T-Scan.pdf 8. Koos B, Godt A, Schille C, Göz G: Precision of an instrumentation-based method of analyzing occlusion and its resulting distribution of forces in the dental arch. J Orofac Orthop. 2010 November; 71(6):403-10. doi: 10.1007/s00056-010-1023-7. Epub 2010 Nov. 17.

9. Sonderforschungsbereich 379, Mikromechanische Sensor- and Aktorarrays, Scanner http://www.zfm.tu-chemnitz.de/pdf/sfb379_finalslides/scan-ner.pdf;Folie

The invention claimed is:

1. A measuring apparatus for measuring at least a part of an oral cavity, with a measuring head, the measuring head comprising
at least two measuring units, wherein each measuring unit comprises a measuring zone and wherein the measuring zones are arrangeable such that they acquire different areas of the oral cavity, and
a carrier carrying the measuring units,
wherein a relative arrangement of the measuring zones of the at least two measuring units is adjustable.

2. The measuring apparatus according to claim 1 wherein the carrier is configurable at least into a first and into a second configuration,
wherein the relative arrangement of the measuring zones in the first configuration differs from the relative arrangement of the measuring zones in the second configuration.

3. The measuring apparatus according to claim 2 wherein at least a part of the carrier is elastically or plastically deformable for configuring, in particular reversibly configuring the carrier from the first configuration into the second configuration and/or from the second configuration into the first configuration.

4. The measuring apparatus according to claim 1 wherein the carrier comprises at least two measuring members movable with respect to each other, wherein at least one of the measuring units is arranged at each measuring member.

5. The measuring apparatus according to claim 1 wherein the measuring head is structured to define a measuring space,
wherein in at least one configuration of the carrier the measuring space is open on both sides along an axis X, is confined along an axis Y on both sides by the measuring head, and is open on one side and confined on one side by the measuring head along an axis Z,
wherein the axes X, Y and Z are orthogonal with respect to each other.

6. The measuring apparatus according to claim 5 wherein the measuring head comprises:
at least two lateral guiding members with guiding zones for laterally abutting on a row of teeth and
at least two lateral measuring members, wherein at least a part of the measuring units is arranged on the lateral measuring members,
and particularly wherein the measuring head is configured or configurable such that along the axis Z the distance of the guiding zones of the lateral guiding members from a part of the measuring head confining the measuring space along the axis Z is between 5 and 20 mm and such that along the axis Y a clearance between the guiding zones of the lateral guiding members is between 10 and 24 mm.

7. The measuring apparatus according to claim 6 wherein the lateral guiding members are movable with respect to each other such that a distance between the guiding zones of the lateral guiding members is variable by at least 3 mm, and particularly wherein the lateral measuring members are movable with respect to each other.

8. The measuring apparatus according to claim 6 wherein the lateral measuring members and/or the lateral guiding members are arranged pivoting with respect to each other, and particularly wherein the lateral measuring members and/or the lateral guiding members are pivoting with respect to each other by at least 30°.

9. The measuring apparatus according to claim 8 further comprising at least one sensor for measuring a pivoting position of the lateral measuring members and/or of the lateral guiding members.

10. The measuring apparatus according to claim 6 wherein the measuring head further comprises a central measuring member,
wherein the lateral measuring members are arranged pivoting on the central measuring member
and particularly wherein
a distance between the lateral guiding members is variable by at least 3 mm and/or
the lateral measuring members are arrangeable crosswise, particularly orthogonal,
with respect to the central measuring member.

11. The measuring apparatus according to claim 10 wherein at least a part of the measuring units comprises optical sensors for three-dimensionally measuring the oral cavity, and
wherein at least a part of the optical sensors is arranged on the central measuring member.

12. The measuring apparatus according to claim 10 wherein the lateral measuring members are pivoting at least between a first position and a second position,
wherein the first position measuring-space-facing angles between each of the lateral measuring member and the central measuring member are at most 90°, and
wherein in the second position the measuring-space-facing angles are at least 135°.

13. The measuring apparatus according to claim 10 further comprising a supporting element arranged on a measuring-space-facing side of the central measuring member,
wherein the supporting element is transparent or recessed in an area of the measuring units.

14. The measuring apparatus according to claim 6 further comprising, an actuator for pivoting the lateral measuring members with respect to each other,
and particularly wherein the measuring apparatus further comprises at least one sensor for controlling the actuator and/or wherein by means of the actuator the lateral measuring members can be pivoted into pre-defined positions.

15. The measuring apparatus according to claim 6 wherein the lateral measuring members extend along the axis X over a length of 3 to 12 mm and/or wherein the lateral guiding members extend along the axis X over a length of 4 to 30 mm.

16. The measuring apparatus according to claim 6 wherein the lateral guiding members are arranged at the lateral measuring members.

17. The measuring apparatus of claim 16 wherein the lateral guiding members are arranged along edges of the lateral measuring members, wherein said edges are located at side of the lateral measuring members opposite to said central measuring member.

18. The measuring apparatus according to claim 1 further comprising a shaft arranged at the measuring head,
wherein the shaft has a length of at least 5 cm.

19. The measuring apparatus of claim 18 further comprising a movable connection arranged between said shaft and said measuring head.

20. The measuring apparatus according to claim 1, further comprising
a support for stabilizing the measuring head on a row of teeth and
a tilting actuator for tilting at least a part of the carrier with respect to the support.

21. The measuring apparatus according to claim 20 wherein the measuring head is structured to define a measuring space,
wherein in at least one configuration of the carrier, the measuring space is open on both sides along an axis X, is confined along an axis y on both sides by the measuring head, and is open on one side and confined on one side by the measuring head along an axis Z,
wherein the axes X, Y and Z are orthogonal with respect to each other, and
wherein the carrier is tiltable with respect to the support around the axis Y and/or the axis Z by means of the tilting actuator.

22. The measuring apparatus according to claim 1 wherein at least a part of the measuring units comprises micro projectors and micro cameras, and
particularly wherein the micro projectors and micro cameras are arranged at the measuring head and/or wherein the micro projectors and micro cameras are arranged alternatingly both line-by-line and column by column.

23. The measuring apparatus according to claim 22 wherein the micro projectors are structured to project a pattern of crossed stripes.

24. The measuring apparatus according to claim 22 wherein the measuring head is structured to define a measuring space,
wherein in at least one configuration of the carrier, the measuring space is open on both sides along an axis X, is confined along an axis Y on both sides by the measuring head, and is open on one side and confined on one side by the measuring head along an axis Z,
wherein the axes X, Y and Z are orthogonal with respect to each other,
wherein the micro projectors and/or micro cameras are arranged at different angular positions with respect to the axis X, and/or
wherein the measuring apparatus further comprises at least one piezo actuator for moving the micro projectors and/or micro cameras individually or in groups.

25. The measuring apparatus according to claim 22 wherein the micro projectors and/or micro cameras have different ranges of depth of field and/or comprise focus-adaptive lenses.

26. The measuring apparatus according to claim 22 wherein at least one surrounded micro camera is arranged between at least three surrounding micro projectors, and wherein the surrounding micro projectors are structured to emit light of different spectral ranges.

27. The measuring apparatus according to claim 22 wherein at least one surrounded micro projector is arranged between at least three surrounding micro cameras, and
wherein the surrounding micro cameras are structured to record a projected pattern of the surrounded micro projector, and
particularly wherein the surrounded micro projector is structured to vary the projected pattern over time.

28. The measuring apparatus according to claim 1 wherein the measuring head comprises at least one true color camera for generating recordings in true color.

29. The measuring apparatus according to claim 1 further comprising at least one contact—or distance sensor for detecting a contact of the measuring head with the oral cavity, and
particularly wherein the measuring apparatus is structured to adjust a configuration of the carrier depending on the signal of the contact—or distance sensor.

30. The measuring apparatus, according to claim 1, for measuring at least a part of a row of teeth with
a measuring head defining a measuring space, the measuring space being open on both sides along an axis X, being confined on both sides along an axis Y by the measuring head and being open along an axis Z on one side and confined on one side by the measuring head,
wherein the axes X, Y and Z are orthogonal with respect to each other, the measuring apparatus further comprising
measuring units for three-dimensionally measuring a region of the row of teeth located in the measuring space,
wherein the measuring head comprises:
at least two lateral guiding members with guiding zones for latterly abutting on the row of teeth, and
at least two lateral measuring members, wherein at least a part of the measuring units is arranged in the lateral measuring members,
and wherein the measuring head is configured or configurable such that along the axis Z a distance of the guiding zones from a part of the measuring member confining the measuring space along the axis Z is between 5 and 20 mm and such that along the axis Y a clearance between the guiding zones of the lateral guiding members is between 10 and 24 mm.

31. A method for measuring at least a part of an oral cavity using an apparatus according to claim 1, the method comprising the steps of
a) positioning the measuring head on a structure of the oral cavity, particularly on a row of teeth, such that the structure is placed in a measuring space defined by the measuring head, and particularly wherein at least lateral guiding members of the measuring apparatus contact the structure,
b) guiding the measuring head along the structure, particularly such that at least one lateral guiding member stays in touch with the structure, and
c) measuring the structure, particularly during the guiding of the measuring head.

32. The method according to claim 31 wherein the measuring apparatus comprises a shaft and an electronically controlled tilting actuator for tilting the measuring head around at least one axis with respect to the shaft, and
wherein the method comprises a further step of, during the measuring of the structure, tilting the measuring head with respect to the shaft into different positions by means of the tilting actuator to generate measurements from different viewing angle positions.

33. The method according to claim 31 wherein a configuration of the carrier is varied during the guiding of the measuring head along the structure.

34. The method according to claim 31 wherein the measuring head as well as a shaft of the measuring apparatus comprises occlusal guiding members for abutting on a row of teeth and wherein during the measuring of the row of teeth the occlusal guiding members occlusally abut on the row of teeth.

35. The method according to claim 34 wherein the measuring head comprises lateral guiding members and wherein the lateral guiding members are brought into abutting against lateral surfaces of teeth of the row of teeth during the measuring or wherein the lateral guiding members are brought into abutting against the oral mucosa of the row of teeth during measuring.

36. The method according to claim 31 wherein during the measuring, the measuring head is guided without settling at least along half of the row of teeth, particularly along the complete row of teeth.

37. The method according to claim 36 wherein the measuring head is guided in two runs from a left into a right region of the oral cavity and from the right into the left region of the oral cavity, or vice versa, and wherein the measuring head is taken off the structure between the two runs, is reversed by 180°, and is positioned on the structure again.

38. The method according to claim 31 wherein the guiding of the measuring head is carried out continuously, and particularly wherein the measuring apparatus comprises an output unit indicating whether a guiding speed is correct, or wherein a displacement of the measuring head during the guiding is carried out intermittently, and in particular wherein the measuring apparatus indicates by means of an output unit when the measuring head is to be advanced further.

39. The measuring apparatus according to claim 1 structured for measuring at least a part of a row of teeth, wherein the measuring zones are arrangeable such that they acquire different areas of the part of the row of teeth.

* * * * *